(12) United States Patent
Rothblatt et al.

(10) Patent No.: US 8,609,728 B2
(45) Date of Patent: Dec. 17, 2013

(54) TREATMENT FOR PULMONARY HYPERTENSION

(75) Inventors: Martine A. Rothblatt, Satellite Beach, FL (US); Lewis J. Rubin, LaJolla, CA (US)

(73) Assignee: United Therapeutics Corporation, Silver Spring, MD (US)

(*) Notice: Subject to any disclaimer, the term of this patent is extended or adjusted under 35 U.S.C. 154(b) by 149 days.

(21) Appl. No.: 13/047,033

(22) Filed: Mar. 14, 2011

(65) Prior Publication Data

US 2011/0224236 A1 Sep. 15, 2011

Related U.S. Application Data

(60) Provisional application No. 61/282,659, filed on Mar. 15, 2010.

(51) Int. Cl.
*A61K 31/19* (2006.01)

(52) U.S. Cl.
USPC .................. 514/569; 514/262.1; 514/269

(58) Field of Classification Search
USPC ..................... 514/262.1, 569, 269
See application file for complete search history.

(56) References Cited

U.S. PATENT DOCUMENTS

| | | | |
|---|---|---|---|
| 4,306,075 A | 12/1981 | Aristoff | |
| 5,153,222 A | 10/1992 | Tadepalli et al. | |
| 5,234,953 A | 8/1993 | Crow et al. | |
| 6,054,486 A | 4/2000 | Crow et al. | |
| 6,469,012 B1 * | 10/2002 | Ellis et al. | 514/234.5 |
| 6,521,212 B1 | 2/2003 | Cloutier et al. | |
| 6,756,033 B2 | 6/2004 | Cloutier et al. | |
| 6,803,386 B2 | 10/2004 | Shorr et al. | |
| 7,199,157 B2 | 4/2007 | Wade et al. | |
| 7,384,978 B2 | 6/2008 | Phares et al. | |
| 7,417,070 B2 | 8/2008 | Phares et al. | |
| 7,544,713 B2 | 6/2009 | Phares et al. | |
| 7,879,909 B2 | 2/2011 | Wade et al. | |
| 7,999,007 B2 | 8/2011 | Jeffs et al. | |
| 8,232,316 B2 | 7/2012 | Phares et al. | |
| 8,252,839 B2 | 8/2012 | Phares et al. | |
| 8,349,892 B2 | 1/2013 | Phares | |
| 8,350,079 B2 | 1/2013 | Walsh | |
| 8,410,169 B2 | 4/2013 | Phares et al. | |
| 2003/0166728 A1 | 9/2003 | Shorr et al. | |
| 2005/0085540 A1 | 4/2005 | Phares et al. | |
| 2005/0165110 A1 | 7/2005 | Wade et al. | |
| 2005/0165111 A1 | 7/2005 | Wade et al. | |
| 2005/0282901 A1 | 12/2005 | Phares et al. | |
| 2005/0282903 A1 | 12/2005 | Wade et al. | |
| 2007/0082948 A1 | 4/2007 | Phares et al. | |
| 2008/0200449 A1 | 8/2008 | Olschewski et al. | |
| 2008/0249167 A1 | 10/2008 | Phares et al. | |
| 2008/0280986 A1 | 11/2008 | Wade et al. | |
| 2009/0036465 A1 | 2/2009 | Roscigno et al. | |
| 2009/0081319 A1 | 3/2009 | Jeffs et al. | |
| 2009/0281189 A1 | 11/2009 | Walsh et al. | |
| 2010/0282622 A1 | 11/2010 | Phares | |
| 2011/0092599 A1 | 4/2011 | Wade et al. | |
| 2011/0118213 A1 | 5/2011 | Phares et al. | |
| 2011/0144204 A1 | 6/2011 | Jeffs et al. | |
| 2011/0224236 A1 | 9/2011 | Rothblatt et al. | |
| 2012/0010159 A1 | 1/2012 | Rothblatt et al. | |
| 2012/0177693 A1 | 7/2012 | Cipolla et al. | |
| 2012/0295980 A1 | 11/2012 | Phares et al. | |

FOREIGN PATENT DOCUMENTS

| | | |
|---|---|---|
| WO | WO 00/54758 A2 | 9/2000 |
| WO | WO 2005/007081 A2 | 1/2005 |
| WO | WO 2007/134292 A2 | 11/2007 |
| WO | WO 2008/049000 A3 | 4/2008 |
| WO | WO 2010/036798 A1 | 4/2010 |

OTHER PUBLICATIONS

Voswinckel et al., Pulmonary Pharmacology & Therapeutic, 2008, 21: 824-832.*

Channick et al., Journal of the American College of Cardiology, 2006, vol. 48, No. 7, pp. 1433-1437.*

Ghofrani et al., Ann. Intern. Med., 2002, 136(7):515-522.*

Gessler et al., 2008, Journal of Aerosol Medicine and Pulmonary Drug Delivery, 21(1): 1-12.*

International Search Report and Written Opinion mailed May 3, 2011, in corresponding PCT/US2011/028390, 16 pages.

Benedict et al., "Evidence-Based Pharmacologic Management of Pulmonary Arterial Hypertension," Clinical Therapeutics, Oct. 2007, 29(10):2134-2153.

Channick et al., "Safety and Efficacy of Inhaled Treprostinil as Add-On Therapy to Bosentan in Pulmonary Arterial Hypertension," Journal of the American College of Cardiology, Oct. 2006, 48(7):1433-1437.

Durongpisitkul et al., "Combination therapy of prostacyclin for pulmonary hypertension in congenital heart disease," Database Embase [Online], Aug. 2005, Database accession No. EMB-2006061495 (abstract of full article published in Journal of the Medical Association of Thailand, Aug. 2005, 88(Supp8):S60-S65).

Ghofrani et al., "Combination Therapy with Oral Sildenafil and Inhaled Iloprost for Severe Pulmonary Hypertension," Ann. Intern. Med., Apr. 2, 2002, 136(7):515-522.

(Continued)

*Primary Examiner* — Rei-tsang Shiao
(74) *Attorney, Agent, or Firm* — Foley & Lardner LLP

(57) ABSTRACT

One embodiment relates to a method of treating pulmonary hypertension based upon co-administering to a subject in need thereof a pharmaceutically effective amount of an oral therapeutic agent for treating pulmonary hypertension and a pharmaceutically effective amount of an inhaled therapeutic agent for treating pulmonary hypertension. The benefit of the co-administration of these agents is to eliminate or reduce one or more side effects associated with mono-therapy of either agent, as well as one or more side effects associated with other administration routes such as subcutaneous or intravenous administration.

4 Claims, No Drawings

(56) References Cited

OTHER PUBLICATIONS

Olschewski, H., "Inhaled iloprost for the treatment of pulmonary hypertension," Eur. Respir. Rev., Mar. 1, 2009, 18(111):29-34.
Opitz et al., "Clinical efficacy and survival with first-line inhaled iloprost therapy in patients with idiopathic pulmonary arterial hypertension," European Heart Journal, Sep. 2005, 26(18):1895-1902.
Voswinckel et al., "Acute effects of the combination of sildenafil and inhaled treprostinil on haemodynamics and gas exchange in pulmonary hypertension," Pulmonary Pharmacology & Therapeutics, Oct. 2008, 21(5):824-832.
U.S. Appl. No. 13/906,585, filed May 31, 2013, Phares et al.
Sandifer et al., "Potent effects of aerosol compared with intravenous treprostinil on the pulmonary circulation," J. Appl. Physiol., Sep. 1, 2005, 99:2363-2368.

* cited by examiner

TREATMENT FOR PULMONARY HYPERTENSION

CROSS-REFERENCE TO RELATED APPLICATIONS

This application claims priority from U.S. Provisional Application Ser. No. 61/282,659, filed Mar. 15, 2010.

All of the publications, patent applications and patents cited in this specification are incorporated herein by reference in their entirety.

BACKGROUND

Pulmonary Arterial Hypertension (PAH) is a condition in which the pressure in the lung circulation increases, eventually causing heart failure and death. Although many causes and conditions are found to be associated with PAH, many of them share in common several fundamental pathophysiological features. One important feature among these processes is dysfunction of the endothelium, the internal cellular layer of all vessel walls, which is normally responsible for the production and metabolism of a large array of substances that regulate vessel tone and repair and inhibit clot formation. In the setting of PAH, endothelial dysfunction can lead to excessive production of deleterious substances and impaired production of protective substances. Whether this is the primary event in the development of PAH or part of a downstream cascade remains unknown, but in either case it is an important factor in the progressive vasoconstriction and vascular proliferation that characterize the disease.

Thus, a need exists to develop an non-invasive therapeutic method to treat PAH.

SUMMARY

One embodiment is a method of treating pulmonary hypertension comprising co-administering to a subject in need thereof a pharmaceutically effective amount of an oral therapeutic agent for treating pulmonary hypertension and a pharmaceutically effective amount of an inhaled therapeutic agent for treating pulmonary hypertension.

An alternative embodiment provides a method of reducing a side effect of a pulmonary hypertension treatment administered by subcutaneous or intravenous delivery, the method comprising co-administering to a subject in need thereof a pharmaceutically effective amount of an oral therapeutic agent for treating pulmonary hypertension and a pharmaceutically effective amount of an inhaled therapeutic agent for treating pulmonary hypertension. The side effect can comprise systemic hypotension, infection, thrombosis, site infusion pain, sudden infusion interruption resulting in death, leg pain, or combinations thereof.

DETAILED DESCRIPTION

Unless otherwise specified, "a" or "an" means "one or more."

The phrase "co-administer" as used herein means that the oral therapeutic agent and the inhaled therapeutic agent are administered so that their effective periods of biological activity will overlap in the subject being treated.

One embodiment is a method of treating pulmonary hypertension comprising co-administering to a subject in need thereof a pharmaceutically effective amount of an oral therapeutic agent for treating pulmonary hypertension and a pharmaceutically effective amount of an inhaled therapeutic agent for treating pulmonary hypertension. In one embodiment, the method reduces or eliminates at least one side effect associated with mono-therapy of either the oral therapeutic agent or the inhaled therapeutic agent or at least one side effect associated with other treatments for pulmonary hypertension, such as subcutaneous or intravenous administration of such agents. For example, the side effect that is eliminated or reduced by one embodiment of the presently described co-administration can include systemic hypotension, infection, thrombosis, site infusion pain, sudden infusion interruption resulting in death, leg pain, or combinations thereof.

The oral therapeutic agent for treating pulmonary hypertension can be selected from the group consisting of treprostinil, beraprost, bosentan, tadalafil, ambrisentan, macitentan, and sildenafil, or a pharmaceutically acceptable salt or ester thereof. The oral therapeutic agent can also comprise a combination of these oral therapeutic agents. In one embodiment, the oral therapeutic agent is treprostinil or a pharmaceutically acceptable salt or ester thereof. Suitable oral formulations of treprostinil are described in U.S. Pat. No. 7,384,978. In one embodiment, the oral therapeutic agent is a diethanolamine salt of treprostinil.

The inhaled therapeutic agent for treating pulmonary hypertension can be selected from the group consisting of treprostinil, Aviptadil, and iloprost, or a pharmaceutically acceptable salt or ester thereof. The inhaled therapeutic agent can also comprise a combination of these inhaled therapeutic agents. In one embodiment, the inhaled therapeutic agent is treprostinil or a pharmaceutically acceptable salt or ester thereof. Suitable inhaled formulations of treprostinil are described in U.S. Pat. No. 6,756,033. In one embodiment, the inhaled therapeutic agent is a sodium salt of treprostinil, which is commercially available as Tyvaso®.

Abnormalities in three major endothelium-based pathways have been identified that serve as the basis for current treatments for PAH:

(1) Overproduction of endothelin. Endothelin is a vasoconstrictor and angiogenic substance that is produced in excess by the injured endothelium in PAH. By blocking the receptor, endothelin-receptor antagonists (ERAs) neutralize the consequences of excessive endothelin synthesis and produce clinical benefit.

(2) Underproduction of Nitric Oxide (NO). Nitric oxide is a potent vasodilator and inhibitor of vascular proliferation that is under produced by the injured pulmonary vascular endothelium in PAH. Nitric oxide mediates these effects through cyclic GMP. By inhibiting the breakdown of the enzyme that catabolizes cGMP, phosphodiesterase type-5 inhibitors (PDE5i) such as sildenafil and tadalafil augment cGMP, thereby minimizing the impact of diminished NO activity in PAH, with resulting clinical benefit.

(3) Underproduction of prostacyclin. Prostaglandins are a heterogeneous family of endoperoxides that are produced in a variety of organ systems and cells and have a number of important regulatory activities. In the vasculature, prostaglandin I2 ($PGI_2$, prostacyclin) is the most abundant and important prostacyclin produced by the endothelium, and serves as a potent vasodilator and inhibitor of growth and proliferation. As with NO, prostacyclin production by the pulmonary vascular endothelium is diminished in the setting of PAH. Treatment of PAH with prostacyclin or its analogues has resulted in clinical benefit in PAH.

Of the various therapeutic approaches to treat PAH currently available, prostacyclin-based therapies are probably the most potent. For example, epoprostenol has been shown to improve survival in PAH. However, these approaches have several shortcomings. Specifically, "prostacyclin replacement therapy" in PAH can be cumbersome, complex and dangerous, because of the pharmacology of the substance. Prostacyclin can be inactivated by a low pH, making it unsuitable for oral administration because the low pH in the stomach can inactivate the compound. Furthermore, the half-life of prostacyclin in the blood is 3-5 minutes, which can demand continuous delivery in order to achieve a sustained pharmacologic effect. Accordingly, epoprostenol (prostacyclin) should be delivered by a continuous intravenous system, using an infusion pump and a permanent catheter inserted into the internal jugular or subclavian vein. Serious complications of this approach can include bloodstream infections, pump malfunction and catheter displacement, and can lead to death.

Alternative approaches to prostacyclin-based therapy can be based on the use of prostacyclin analogues, such as treprostinil and iloprost. Treprostinil, a longer-acting analogue, can be delivered intravenously and subcutaneously, although the former approach has the same limitations as epoprostenol and the latter approach is limited by site pain. The utilization of the lung as a site of delivery of prostacyclin therapy can be desirable: firstly, the lung vasculature is the site of the disease, and the proximity of the alveolar space to the vasculature would allow a greater concentration of drug at the disease site when given by the inhaled route as compared to the systemic route. Secondly, the large surface area of the lung and its vasculature can promote ready absorption of drug into the systemic circulation to facilitate adequate drug circulation and distribution. Both treprostinil and iloprost are approved for inhaled delivery in PAH.

One limitation to inhaled prostanoid therapy in PAH alone is the ability to deliver sufficient drug to equate to the amounts that can be delivered by the parenteral route. Doses higher than those approved for inhaled iloprost or treprostinil are poorly tolerated due to local irritant effects in the airways and rapid uptake by the systemic circulation, leading to intolerable side effects. Patients who deteriorate with inhaled therapy may still respond to parenteral therapy. This suggests that greater amounts of prostacyclin are needed for these patients than can be effectively delivered by the inhaled route alone.

Oral prostacyclin analogues, when used alone, can be less sensitive to gastric pH, but their bioavailability can be poor. Beraprost, an oral prostacyclin analogue, can be limited in its ability to produce long-term benefit in PAH, largely due to the inability to deliver sufficient drug into the circulation without producing intolerable local gastrointestinal side effects. Treprostinil is undergoing clinical trials as an orally-delivered prostacyclin analogue for PAH, but tolerability in doses intended to produce therapeutic blood levels has been a limiting factor thus far.

The drawbacks of the treatments described above can be overcome by utilizing together two noninvasive portals for drug availability. Such a combination may be more efficacious than either route alone and may more closely approximate the efficacy of parenteral therapy without its inherent toxicities. In particular, in one embodiment, a combination of inhaled and oral delivery can be used. In one embodiment, at least two pharmaceutical compositions are delivered into a subject in need thereof by two different routes. The compositions can be the same or different. This combination can overcome the challenges facing prostacyclin-based therapy regarding the toxicity of parenteral delivery and he limited ability to deliver sufficient amounts of effective drug by the nonparenteral route.

Prostacyclin

The prostacyclin used in the therapy as described above can be any type of prostacyclin ($PGI_2$), or an analogue thereof, known in the art, such as any one in the eicosanoid family. In one embodiment, it can be any prostacyclin and/or its analogue that is suitable to treat symptoms of PAH. For example, the prostacyclin can be epoprostenol, treprostinil, iloprost, beraprost, an analogue of any thereof, or combinations thereof. Beraprost can be used to effect vasodilation, which in turn can lower the blood pressure. Beraprost can also inhibit platelet aggregation.

Depending on the chosen delivery routes, different or same pharmaceutical compositions can be used in the embodiments. For example, in one embodiment of the therapy, a combination of beraprost and treprostinil can be used. Specifically, in an embodiment of combined therapy, a first pharmaceutical composition delivered orally to a subject can comprise a prostacyclin, such as beraprost, and a second pharmaceutical composition delivered by inhalation to a subject can comprise prostacyclin, such as treprostinil.

Combined Therapy

In one embodiment, the co-administration can be carried out with any combination of the oral and inhalation agent, as described above. For example, the oral delivery agent can be treprostinil, and the inhalation agent can be iloprost or Aviptadil. Preferably, in one embodiment, the inhaled therapeutic agent is Tyvaso or a pharmaceutically acceptable salt or ester thereof, and the oral delivery agent is bosentan or a pharmaceutically acceptable salt or ester thereof. In an alternative embodiment, the inhaled therapeutic agent is Tyvaso or a pharmaceutically acceptable salt or ester thereof, and the oral delivery agent is sildenafil or a pharmaceutically acceptable salt or ester thereof.

The timing of the co-administration can vary, depending on the need of the patient. For example, the inhalation can be given four times a day, while the oral delivery can be given twice a day. For example, two of the oral dosings can coincide with two of the four inhalations. Alternatively, they do not need to coincident for the therapeutic benefit. In an alternative embodiment, the inhalation can be given at a frequency other than four, such as one, two, three, five, or more, and the oral delivery can be given at a frequency other than two, such as one, three, four, or more. As described above, the administration of the inhalation and oral delivery can overlap but does not need not.

Because almost all the blood circulates through the lungs, if the lungs become too constricted, the blood can have difficulty becoming properly oxygenated and circulating through the lungs. This problem can be aggravated with pulmonary hypertension because the patients platelets are also excessively adhesive to the pulmonary artery walls. Thus, the combined effect of pulmonary artery constriction and platelet adhesion greatly restricts blood flow through the pulmonary arteries, causing the right side of the heart to dilate as it tries to pump hard enough to force blood through to the alveoli, ultimately resulting in right heart failure. The presently described combined therapy can effectively eliminate or alleviate such problem.

In one embodiment, the combined therapy aims for the inhalation to provide a potent vasodilation of the pulmonary arteries and for the oral delivery to provide an desirable antiplatelet benefits, such as preventing the platelets from becoming too adhesive to the pulmonary arterioles. The dosage of the respective inhalation and oral delivery agent can be optimized such that the inhalation can provide the maximum vasodilation effect on the patient's pulmonary arteries and the oral delivery agent can provide the optimal anti-platelet benefit. Other benefits that can be provided by the present combined therapy, as described before, can included systemic hypotension, infection, thrombosis, site infusion pain, sudden infusion interruption resulting in death, or leg pain.

The invention is further illustrated by, though in no way limited to, the following examples.

EXAMPLES

Example 1

The new guideline for the diagnosis and treatment of PAH by Galie et al., 2009, which is hereby incorporated by reference in its entirety, emphasizes the need for investigating combination therapy. The results presented herein can be considered of medical importance because it will be the first authorized combination therapy, fulfilling such medical need. Also, the pathogenesis of PAH is not fully understood, and the rationale of a combination therapy targeted against two different pathophysiological pathways appears plausible, especially in such a fatal disease like PAH.

The combination of Tyvaso with either bosentan or sildenafil did not show relevant pharmacokinetic (PK) interactions, increasing the feasibility of such a combination where no dose adjustments are anticipated. This is in contrast to the PK interactions seen when sildenafil and bosentan, or tadalafil and bosentan are co-administered. The clinical experience with other prostanoids, in particular Remodulin (SC infusion) and Ventavis (inhalation), further supported the efficacy of treprostinil, though as a monotherapy. Tyvaso had one advantage of easier application than Remodulin, and the better compliance thereof than with Ventavis was expected because of lesser daily applications. However, the target population who can benefit from this combined therapy can be better defined.

Patient status can be defined as: stable satisfactory, stable and not satisfactory, or unstable and deteriorating. It can be assumed that patients recruited in TRIUMPH were "stable and not satisfactory" patients based on their 6-MWT of around 350 m and WHO FC III. If this assumption is correct, then the combination therapy has not really achieved the desirable goal (i.e., stable and satisfactory status as defined by the guidelines), but rather, it only improved exercise capacity (and as proposed in the indication). This can be acceptable as outlined before, after adequately defining the target population in as clinically stable patients. This also prevents using Tyvaso as a substitute for epoprostenol, which is the first choice in the more severe or unstable patients.

Considering that treprostinil is the same active constituent in both the SC preparation and the inhalation, several issues need to be addressed. Following the registration of Remodulin SC and through actual clinical experience, it appeared that the effective dose lied above that used in the pivotal clinical studies, which was approximately 10 ng/kg/min. The typical range of Remodulin doses in current clinical practice is estimated to be approximately 20-100 ng/kg/min, with a mean of 53 ng/kg/min. As observed by the present inventors, this need for continuous dose escalation with chronic use is only seen with continuous infusion. One possible explanation for this difference is the functionality of the prostacyclin receptors in the face of continuous versus intermittent drug exposure, where tolerance is more seen with the former method.

This explanation appears plausible, considering that the long term extension study was not actively controlled, and the need for dose escalation can not be excluded. In the long term open-label extension TRIUMPH study, doses up to 72 µg q.i.d. have already been utilized. The possibility of using even higher doses, as is currently practiced with Remodulin, can not be excluded. However, an adequate warning should be added to remedy any lack of safety data. In conclusion, the efficacy of treprostinil inhalation is based on the results of one pivotal trial, which showed a statistically significant increase in the 6-MWD in patients administered treprostinil inhalation on top of bosentan or sildenafil. The combination fulfils an unmet medical need for a combination therapy, but the target group should be defined as clinically stable patients.

Example 2

The placebo-controlled phase of TRIUMPH showed that administration of Tyvaso on top of bosentan or sildenafil resulted in a significant median improvement of +21.6 meters in 6-MWD, as compared to +3.0 meters in the placebo group. This was accompanied by improvement in the level of NT-Pro-BNP, and in some scores of Quality of Life, but not in the functional class or time to clinical worsening. With a study duration of 12 weeks, no significant effects in the latter endpoints were actually expected.

Long term data support the long term durability of the results, though they are difficult to interpret considering the uncontrolled design.

Tyvaso is the first application for combination therapy in the management of PAH. The documented increase in the 6-MWT is in line with that shown with other combinations, in particular iloprost on existing bosentan therapy, sildenafil on top of epoprostenol, and tadalafil on top of bosentan. The current results is considered of medical importance because it will be the first authorized combination therapy, fulfilling such medical need. Also the pathogenesis of PAH is not fully understood and the rationale of a combination therapy targeting two different pathophyisiological pathways appears plausible, especially in a fatal disease like PAH. The combination of Tyvaso with bosentan or sildenafil did not show relevant PK interactions, increasing the feasibility of such a combination where no dose adjustments are anticipated. This is contrast with the PK interactions seen when sildenafil and bosentan, or tadalafil and bosentan are co-administered. The clinical experience with other prostanoids in particular Remodulin (SC infusion) and Ventavis (inhalation) lends further support to the efficacy of treprostinil, though as a monotherapy. Tyvaso has an obvious advantage of easier application than Remodulin, and the present inventors expect better compliance than with Ventavis because of lesser daily applications. However, the target group of this combination therapy with Tyvaso should be adequately defined as clinically stable patients, to prevent using Tyvaso as a substitute for epoprostenol which is specifically indicated for unstable patients.

The combination of Tyvaso with either bosentan or sildenafil (two oral PAH treatments) appears feasible as it targets two different pathophysiological pathways. No PK interactions are seen. The gain in the 6 MWT is moderate but in line with other combinations. Efficacy of Tyvaso is also supported by the efficacy previously shown for Remodulin or Ventavis. It promises in addition easier and less frequent application. However, as with other prostanoids, tolerance to the effect and the need of higher doses with chronic administration can not be excluded.

No conclusions is yet drawn regarding the superiority of Tyvaso when combined with bosentan compared to when it is combined with sildenafil. The combination of Tyvaso with either drug is acceptable, provided that the target group is adequately defined as clinically stable patients and the expected treatment goals are clear.

Example 3

Remodulin® (treprostinil sodium) Injection has been approved in the United States and other countries for continuous subcutaneous and intravenous infusion for the treatment of pulmonary arterial hypertension (PAH). Tyvaso® (treprostinil) Inhalation Solution has also been approved in the United States for the treatment of PAH. Treprostinil is a chemically stable tricyclic benzindene analogue of prostacyclin (PGI2) that exhibits platelet anti-aggregatory and potent vasodilatory effects. UT-15C is the diethanolamine salt of treprostinil, currently in development by United Therapeutics Corporation as a sustained release oral treatment option for PAH.

Summary: Given that the identical bioactive molecule, treprostinil, is delivered by each of these routes of administration, the present study was undertaken to help determine whether combined treatment with oral plus inhaled treprostinil (UT-15C plus Tyvaso) may have additive effects on cardiopulmonary hemodynamics in a rat PAH model. It would be clinically desirable if combined oral plus inhaled dosing could prevent, or delay the time to initiation of parenteral therapy, which is the most invasive route and is typically reserved for the advanced disease.

This study utilized administration of a thromboxane agonist to elevate pulmonary artery pressure (PAP) in the rat as a model for PAH. Treprostinil was administered to the rats by oral gavage (UT-15C), nose-only inhalation (Tyvaso) or in a combined oral+inhalation regimen, followed by PAP assessment. In this initial experiment in a newly developed rodent PAH model to monitor PAP measurements during treprostinil therapy, treprostinil therapy generally reduce PAP during the PAH condition, regardless of the route of administration. Also, additional PAP reduction was observed (either in magnitude or duration) when oral treprostinil was administered in addition to a low dose of inhaled treprostinil as part of a combination dosing regimen.

Experimental Design: For this study, a rat model of acute PAH was developed with the ability to measure real-time PAP by telemetry from a catheter surgically implanted into the rat pulmonary artery. To induce PAH in this model, a 15 minute intravenous (IV) infusion of the thromboxane agoinst, U44069, was administered, and PAP was monitored and recorded every 5 seconds.

To establish this model, initial testing and optimization of the concentration and infusion rate of the U-44069 was performed to best achieve elevated PAP. Preliminary dose range-finding assessments of the efficacy of oral or inhaled treprostinil at doses that have previously been shown to have limited toxicities in GLP preclinical animal studies were also performed. Following the preliminary individual oral and inhaled treprostinil range-finding studies, a combination administration of oral+inhaled treprostinil was performed. The study design and results are described below.

Study Design

| Group Number | Group Designation | Target Dose Level For gavage (mg/kg/day) | Formulation Concentration for Gavage (mg/mL) | Target Dose Level[4] For inhalation (μg/kg/day) | Duration of inhalation exposure (min) | Number of Animals Male |
|---|---|---|---|---|---|---|
| 1 | Low Dose | 5 | 1 | 5.26 | 9 | 2 |
| 2 | Mid Dose | 10 | 2 | 10.6 | 17 | 2 |
| 3 | High Dose | 15 | 3 | 34.1 | 55 | 2 |

[4]Target dose levels are calculated based on an estimated body weight of 0.3 kg.

IV Dose of U-44069 to Elevate PAP:

The animals received U-44069 (0.5 mg/mL) at a dose rate of 10 mL/kg/hr for 15 minutes for a total dose of 1.25 mg/kg/dose. The animals received 3 to 4 IV doses/session, as detailed below.

Dose 1, Oral Gavage:
1. Animals were treated as follows:
2. IV for 15 minutes
3. Oral gavage, as soon as practicable following the 15-minute infusion
4. 1 hour following gavage, IV for 15 minutes.
5. 2 hours following gavage, IV for 15 minutes Dose 2, Inhalation:
Animals were treated as follows:
1. IV for 15 minutes
2. Inhalation exposure, as soon as practicable following the 15-minute infusion
3. Approximately 5 minutes after inhalation completion, IV for 15 minutes.
4. 1 hour later, IV for 15 minutes Dose 3, Inhalation and Oral Gavage:
Animals were treated as follows:
1. IV for 15 minutes
2. Oral gavage, as soon as practicable following the 15-minute infusion
3. Inhalation exposure, as soon as practicable following oral gavage. All animals were exposed to the low dose (5.26 μg/kg).
4. Approximately 5 minutes after inhalation completion, IV for 15 minutes.

5. 1 hour later, IV for 15 minutes
6. 2 hours after oral gavage, IV for 15 minutes for 2 animals (1 low and 1 high oral dose)

Inhaled, Oral and Combination Treprostinil Dosing Results:

The following figure summarizes the results from the separate routes or combination administration of treprostinil for the individual telemetered animals. Maximum PAP values during the U-44069 infusions are expressed as the % change from baseline (untreated) PAP.

On all reported occasions, the IV dosing of U-44069 increased the PAP to at least 150% of the baseline, except for animal 2001. However, it should be noted that the baseline pressures for this animal are significantly higher than the other animals.

Inhalation—5.26, 10.6, or 34.1 µg/kg/day : PAP was reduced to approximately 120% the baseline following inhalation exposure at all dose levels and was relatively stable over the 15-minute injection. Following an additional IV injection of U-44069 1-hour after the completion of inhalation exposures, PAP was significantly increased when compared to the Immediately Post Dosing (IPD) values. At 1 hr post dosing (PD), PAP was significantly increased when compared to the IPD values.

Oral gavage—5, 10, or 15 mg/kg/dose: decreases in PAP were generally observed in a dose-related fashion at both the 1 hr PD and 2 hr PD time points evaluated.

Combination Dosing—low dose inhaled (5.26 µg/kg/day)+low (5 mg/kg/dose), mid (10 mg/kg/dose), or high (5 mg/kg/dose) dose oral gavage:

Group 1: Combination dosing of treprostinil exhibited a sustained effect to 1 hr that was not seen when only low dose inhaled treprostinil was administered. The sustained reduction in PAP was likely more apparent in animal #1001 because the U-44069 had a greater pharmacological effect on increasing PAP in this animal, and the action of treprostinil to reduce PAP toward baseline values was more apparent.

Group 2: For both animals, the PAP decrease was equivalent or greater at the IPD time point, even though the low inhaled dose (5.26 µg/kg/day) in the combination dosing regimen is half of the individual mid-dose inhalation (10.6 µg/kg/day). For animal #2002 the increased PAP reduction was sustained out to 1 hr PD and this reduction was even greater than the individual oral dose. For animal #2001, the reduction in PAP was greater (possibly additive) at the IPD and slightly lower at 1 hr PD when compared to the individual mid dose inhalation, although it was slightly higher than the oral alone at 1 hr PD. This could be due to variability in this animal. In addition, the U-44069 had a greater pharmacological effect on increasing PAP in animal #2002, which likely allowed for a greater action of treprostinil to reduce PAP toward baseline values.

Group 3: Even though the low inhaled dose (5.26 µg/kg/day) in the combination dosing regimen is less than 6x the high dose (34.1 µg/kg/day) administered in the individual inhalation condition, the ability of the combination dosing regimen to reduce PAP at the IPD time point was equivalent (#3001) or greater (#3002) than the individual high dose inhalation, and this effect was sustained out to 1 hr PD. The U-44069 had a greater pharmacological effect on increasing PAP in animal #3002 during the combination dosing component, which likely allowed treprostinil to better reduce PAP at the IPD time point.

For combination dosing, it also appeared that animals that responded well to treprostinil via inhalation and not as well to treprostinil via oral gavage (#1001 and #2002) were better able to show a sustained effect at 1 hr PD during the inhalation therapy. More refined dose range-finding studies (dosing and time points for PAP measurements) will help us to better understand this observation.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

What is claimed is:

1. A method of treating pulmonary hypertension comprising co-administering to a subject in need thereof a pharmaceutically effective amount of an oral therapeutic agent for treating pulmonary hypertension and a pharmaceutically effective amount of an inhaled therapeutic agent for treating pulmonary hypertension, wherein the oral therapeutic agent is treprostinil or a pharmaceutically acceptable salt or ester thereof and wherein the inhaled therapeutic agent is treprostinil or a pharmaceutically acceptable salt or ester thereof.

2. The method of claim 1, wherein the subject is a human being.

3. The method of claim 2, wherein the co-administration delays the time to initiation of parenteral therapy for pulmonary hypertension in comparison to therapy with either an oral or inhaled therapeutic agent for pulmonary hypertension used alone.

4. The method of claim 1, wherein the oral therapeutic agent is the diethanolamine salt of treprostinil and the inhaled therapeutic agent is the sodium salt of treprostinil.

* * * * *